US012057202B2

(12) United States Patent
Lopez et al.

(10) Patent No.: US 12,057,202 B2
(45) Date of Patent: Aug. 6, 2024

(54) PROCEDURE FOR UNIFIED GLOBAL REGISTRY AND UNIVERSAL IDENTIFICATION OF PRODUCTS OF BIOLOGICAL ORIGIN FOR MEDICINAL PURPOSES

(71) Applicant: CONNECTING SOLUTION & APPLICATIONS LTD., Vancouver (CA)

(72) Inventors: Fernando Latorre Lopez, Soria (ES); Nuria Sala Cano, Soria (ES)

(73) Assignee: CONNECTING SOLUTION & APPLICATIONS LTD., Vancouver (CA)

( * ) Notice: Subject to any disclaimer, the term of this patent is extended or adjusted under 35 U.S.C. 154(b) by 743 days.

(21) Appl. No.: 17/187,547

(22) Filed: Feb. 26, 2021

(65) Prior Publication Data

US 2021/0183479 A1    Jun. 17, 2021

Related U.S. Application Data

(63) Continuation-in-part of application No. 16/169,126, filed on Oct. 24, 2018, now abandoned.

(51) Int. Cl.
*G16H 10/40* (2018.01)
*G16H 15/00* (2018.01)
(Continued)

(52) U.S. Cl.
CPC ............ *G16H 10/40* (2018.01); *G16H 15/00* (2018.01); *G16H 70/00* (2018.01); *G16H 80/00* (2018.01)

(58) Field of Classification Search
None
See application file for complete search history.

(56) References Cited

U.S. PATENT DOCUMENTS

| 2002/0119769 A1* | 8/2002 | Heinonen | G01W 1/04 455/423 |
| 2003/0004751 A1* | 1/2003 | Ng | G16H 15/00 705/2 |

(Continued)

FOREIGN PATENT DOCUMENTS

| EP | 2290571 A1 | 3/2011 |
| ES | 2615815 A1 | 6/2017 |

(Continued)

OTHER PUBLICATIONS

PCT, Written Opinion and International Search Report of International Application No. PCT/CA2022/050276, mailing date May 18, 2022.

(Continued)

*Primary Examiner* — Robert A Sorey
(74) *Attorney, Agent, or Firm* — Norton Rose Fulbright Canada LLP; Maya Medeiros

(57) ABSTRACT

A procedure for the unified global registry and universal identification of products of biological origin for medicinal purposes is described. The method includes generation of a global and unique data storage vault for each product and related parties, one or more local data vaults associated with the global storage vault, one or more data profiles associated with the vaults, a unique and non-transferable public and private identifier associated with the global storage vault, one or more alphanumeric-hexadecimal translation maps associated with the public and private identifier, and a unique and non-transferable public identification code. The method further includes storing data in a database accessible by different parties depending on the data access rights. The method further includes identification of the data storage vault and the type of data stored through the unique and (Continued)

non-transferable identification code and automatically updating the information in the vaults and profiles stored in the database.

13 Claims, 3 Drawing Sheets

(51) Int. Cl.
    *G16H 70/00*     (2018.01)
    *G16H 80/00*     (2018.01)

(56) References Cited

U.S. PATENT DOCUMENTS

| | | | |
|---|---|---|---|
| 2003/0187821 A1 | 10/2003 | Cotton et al. | |
| 2006/0136390 A1* | 6/2006 | Zhao | G06F 16/9014 |
| 2007/0004969 A1* | 1/2007 | Kong | A61B 5/0205 |
| | | | 128/920 |
| 2007/0219826 A1* | 9/2007 | Brodsky | G06Q 10/00 |
| | | | 705/2 |
| 2009/0187583 A1 | 7/2009 | Pape et al. | |
| 2012/0297255 A1 | 11/2012 | Case et al. | |
| 2013/0111166 A1 | 5/2013 | Resch et al. | |
| 2013/0111609 A1* | 5/2013 | Resch | G06F 11/1076 |
| | | | 726/29 |
| 2016/0267489 A1 | 9/2016 | Hodges | |
| 2017/0056677 A1 | 3/2017 | Zhang et al. | |
| 2018/0068073 A1 | 3/2018 | Kaneko | |
| 2018/0114592 A1* | 4/2018 | Apte | G16B 20/40 |
| 2018/0247346 A1 | 8/2018 | Latorre Lopez et al. | |
| 2018/0292221 A1* | 10/2018 | Bastide | G06N 5/022 |
| 2018/0293478 A1 | 10/2018 | Cannell et al. | |
| 2019/0096532 A1 | 3/2019 | Dodge | |
| 2019/0156925 A1* | 5/2019 | Martinez-Arocho | |
| | | | G16H 15/00 |
| 2019/0253254 A1* | 8/2019 | Brownlee | G06K 19/0725 |
| 2020/0135305 A1 | 4/2020 | Latorre Lopez et al. | |

FOREIGN PATENT DOCUMENTS

| | | | | |
|---|---|---|---|---|
| WO | WO-2005097190 A2 * | 10/2005 | | C12N 5/0605 |
| WO | 2007014147 A2 | 2/2007 | | |
| WO | 2014186559 A2 | 11/2014 | | |

* cited by examiner

PROCEDURE FOR UNIFIED GLOBAL REGISTRY AND UNIVERSAL IDENTIFICATION OF PRODUCTS OF BIOLOGICAL ORIGIN FOR MEDICINAL PURPOSES

CROSS-REFERENCE TO RELATED APPLICATIONS

This application Continuation-in-Part of pending U.S. patent Ser. No. 16/169,126 filed on Oct. 24, 2018, the entirety of which is hereby fully incorporated herein by reference.

FIELD OF THE INVENTION

The present invention is generally encompassed in the health sector. More specifically, in donations, manufacture of medicines of biological origin, and tissue engineering and data management, falling particularly in the field of: centers for the obtention or collection of donations of blood, plasma, cells, tissues and organs, centers or laboratories for the generation of tissues and organs; centers destined to carry out transplants and transfusions, pharmaceutical companies producing blood products, laboratories for the production of medicines of biological origin, and data management systems. More particularly the invention relates to a procedure for the unified global registry and universal identification of products of biological origin for medicinal purposes in humans or in other living beings and of the different related parties.

BACKGROUND

Obtaining and using materials and products of biological origin involves certain specific considerations arising from the nature of the products and the processes. The ways in which biological products are obtained, manufactured, controlled and administered make some particular precautions necessary. The obtention or manufacture of products of biologic origin may involve processes such as cultivation of cells or the extraction of products from living organisms and carry a risk of transmission of diseases. While this risk is minimized through testing and processing, it can never be completely eliminated (e.g. the detection of a serious infectious disease in a donor after having made one or more donations of one or more types over time).

Worldwide, 112 million donations of blood and plasma of human origin are collected annually and more than 120,000 human organ transplants are performed, although the WHO recognizes that this figure is only 10% of the transplants that are necessary each year. In addition, the average life of a transplanted organ is 10 years if it comes from a deceased human donor and from 14 years if it comes from a living donor.

Some of the products of biological origin for medical purposes, such as blood and its derivatives or organs, have a very short shelf life and have to be kept under very strict temperature conditions to ensure their quality and that they do not suffer deterioration. For example, each blood donation is fractionated to separate its components (red blood cells, plasma and platelets mainly) and make blood products (products derived from blood). A unit of red blood cells (RBC) is obtained from 3 blood donations and an expiration of up to 42 days is achieved using preservatives such as Sagmanitol, provided that it remains between 1 and 6 Celsius degrees, although there are studies that claim that Red blood cell deterioration occurs as the time since the blood was collected increases. In the case of platelets, the expiration is from 5 to 7 days. The plasma can be maintained for up to 2 years at a temperature of 30 degrees centigrade below zero. Tissues and organs such as the heart or lung have an average preservation time of between 3 and 5 hours after extraction, while skin and bones can be preserved for up to 5 years.

Some blood products, such as units of red blood cell (RBC) or platelets (PLT), are usually not sent to other countries except in some emergency cases. However blood plasma is exported from the U.S. to the rest of the world to manufacture drugs such as vaccines or hemophilia medications from immunoglobulins. In fact, approximately 65% of the global plasma comes from the U.S. and nearly half of the U.S. plasma is exported to Europe.

A donor can be the source of many different products. For example, a deceased donor can donate skin, tendons, heart valves and a wide range of bone products. All these different products share a common history. Some of the products obtained from a donor may fall within the regulation of biological products, while other products from the same donor may correspond to the regulation of medical devices or even not be considered medicines (e.g. creams).

Biological products are products of biological origin. They include a wide range of products such as vaccines, blood and blood components, allergenics, somatic cells, gene therapy, tissues, and recombinant therapeutic proteins. Biological products can be composed of sugars, proteins, or nucleic acids or complex combinations of these substances, or may be living entities such as cells (ovules, red blood cells, . . . ), tissues and organs. They are isolated from a variety of natural sources (human, animal, vegetable, microorganism) and may be produced by biotechnology methods and others technologies.

For biological medicinal products, starting materials shall mean any substance of biological origin such as microorganisms, organs and tissues of either plant or animal origin, cells or fluids (including blood or plasma) of human or animal origin, and biotechnological cell constructs (cell substrates, whether they are recombinant or not, including primary cells). A biological medicinal product is a product, the active substance of which is a biological substance. A biological substance is a substance that is produced by or extracted from a biological source and that needs for its characterization and the determination of its quality a combination of physico-chemical-biological testing, together with the production process and its control.

The manufacture of biological medicinal products is a highly demanding process. Protein-based therapies have structures that are far larger, more complex, and more variable than the structure of drugs based on chemical compounds. Plus, protein-based drugs are made using intricate living systems that require very precise conditions in order to make consistent products. The manufacturing process consists on producing the master cell line containing the gene that makes the desired protein, growing large numbers of cells that produce the protein, isolating and purifying the protein and preparing the biologic for use by patients. Some biologics can be made using common bacteria, others require cell lines taken from mammals Each biotechnological process starts with the creation of a unique cell line to develop the desired medicine and at each stage of this process, the biological medicine acquires a series of properties that make it different from the rest. Therefore, due to the great diversity of factors that can vary in the process of obtaining these drugs, the final activity in vivo can be altered, either by experiencing reductions in the therapeutic effect or by the appearance of immunogenicity.

Biological drugs have some potential to be recognized by the body as foreign substances and, consequently, have the inherent ability to induce unwanted immune reactions due to their composition and their high molecular weight. One of the most important issues in the appearance of immunogenicity reactions is the possible variation in the glycosylation pattern experienced by this type of drugs, which can lead to unpredictable clinical consequences. This potential to induce immunogenicity on the part of biological medicines is why pharmacovigilance and the traceability of these medicines acquire special importance, with the aim of ensuring and promoting their safe use.

Biosimilar medicines are defined as biological products "similar" to other biotechnological medicines already authorized, produced by a different manufacturer of the biological reference drug, using different cell lines, different processes and analytical methods. Although the biological substance of a biosimilar and its reference medicine is essentially the same, there may be certain differences related to its complex nature and method of elaboration. Due to the complex process, hundreds of irreproducible phases to which the different cell lines are subjected, it is impossible to guarantee the production of completely identical biological products.

The inclusion of batch and lot records allows the rapid detection of any problem related to specific lots or batches of a product and allows the grouping of medicines by shared attributes (such as active pharmaceutical ingredient), brand name or manufacturer, specific lots and batches of a sole medicinal product. The maximum combination of data can lead to more timely decisions in pharmacovigilance.

There are different labeling systems for products such as ISBT, HIBC or GS1. Currently the products of biological origin obtained in a certain center carry a product identification code generated by one of these systems. In addition, different unified codes for medical devices (UDI) have been implemented currently in some countries and are being developed in others to achieve a better traceability of the products in each territory. However, these UDIs are independent and different of each other and their databases are intended to be isolated (Europe, USA, Australia, . . . ). On the other hand, and apart from the UDI, other products of biological origin have to be identified with other specific codes such as the Single European Code (SEC) for tissues and cells in Europe.

In addition to the above, the traceability of the origin of biological materials or products are limited at the level of a specific organization or territory, due to the isolation of existing data between different systems, organizations and territories, as in the case of donors or recipients. Until now, the identifier of a blood or organ donor was at the local level for a public or private organization or for a specific territory. The same happens with an individual recipient of a tissue or organ transplant, of a transfusion of blood products such as red blood cells or of a vaccine in which blood plasma has been used in the manufacture, since the identification and traceability of the individual is currently a local code of user, client or patient for a specific public or private medical or hospital organization or a health code for a territory, whose history is isolated from other centers or territories.

The application US-2018-0247346-A1, which in turn is a continuation of the patent PCT/ES2016/070428 and which in turn is a continuation of the patent in Spain P201531611, now allows a unified global registry of blood donors and other types to be available. This makes knowledge of the history of a donor in any donation center possible and thus improve the traceability and safety of suppliers of these biological products in different public or private organizations and in different territories. This also allows knowledge of other relevant health data related with the donor, which makes it possible to improve the safety of the products (frozen plasma unit, tissues, organs, . . . ) and a universal traceability from donor to recipient, together with the possibility of minimizing the illegal black market of certain products.

However, there is no known global system that allows the monitoring of the recipients of products of biological origin (transfusion, transplant, vaccination, . . . ) beyond the organization or specific territory where the process is carried out, and that can allow a universal traceability from recipient to donor in an automatic way. There is also no known global system to register the use of products of biological origin in a unified record of clinical interventions or treatments of this type and that can allow traceability of centers, products used and recipients thereof (users, clients or patients). For example, in a clinical intervention to perform a tissue implant, transfusions of blood products may be required, but there is no known unified system that allows a global automatic post-traceability of the products of biological origin used in a specific recipient, client, user or patient, as in the event that some kind of adverse effect occurs in the short, medium or long term and the recipient is treated in a medical center of another organization and/or different territory. There is also no known unified global system to automatically alert to this individual and/or to the medical reference center of an anomaly detected in one of these products to take the appropriate actions.

On other hand, labeling products with printed labels has some drawbacks. For example, the label may be misplaced in a similar product or may deteriorate and hinder product identification. This is very important for example when labeling blood bags, as each blood bag has to be associated with a specific donor with a specific blood group and is also associated with a blood sample tube with which blood tests are performed to find out if the donated blood is valid or has to be discarded according to the blood test result.

Nevertheless every NFC chip has a globally unique, manufacturer supplied, read-only identifier (UID) that can be read by most NFC devices. An NFC tag's UID cannot be changed or erased; it is stored in special memory in the NFC chip which does not allow the bits to be changed. So this technology can be used to identify a product worldwide, such as a donated pint of blood, and also can be associated with the internal common identifier given for the donation centers to commonly identify donors when using the unified registry of donors.

The classification of medical devices bind manufacturers to determine the product classification in order to comply the Medical Device Directives, For example, blood, human cells, tissues or organs intended for implantation, transplantation, infusion, or transfer into a human recipient are regulated as medical devices in some countries. But the Medical Device Directives are different in each country.

A Medical Device, as is described by the International Medical Device Regulators Forum (IMRF), means any instrument, apparatus, implement, machine, appliance, implant, reagent for in vitro use, software, material or other similar or related article, intended by the manufacturer to be used, alone or in combination, for human beings, for one or more specific medical purpose(s). Some products may be considered to be medical devices in some jurisdictions but not in others, as devices incorporating animal and/or human tissues, for example.

In Europe, as in the above reference, the definition of Medical Device only include humans as recipients, not animals But the Food and Drug Administration (FDA) define medical device for pre-marketing and post-marketing regulatory controls in this way: "an instrument, apparatus, implement, machine, contrivance, implant, in vitro reagent, or other similar or related article, including a component part, or accessory which is:

recognized in the official National Formulary, or the United States Pharmacopoeia, or any supplement to them, intended for use in the diagnosis of disease or other conditions, or in the cure, mitigation, treatment, or prevention of disease, in man or other animals, or intended to affect the structure or any function of the body of man or other animals, and which does not achieve its primary intended purposes through chemical action within or on the body of man or other animals, and which does not achieve its primary intended purposes through chemical action within or on the body of man or other animals and which is not dependent upon being metabolized for the achievement of its primary intended purposes. The term "device" does not include software functions excluded pursuant to section 520(o).

So animals are included as recipients by the FDA, not by the IMRF nor the E.U. Also, distinctions are made between a medical device and other regulated products such as drugs. If the primary intended use of the product is achieved through chemical action or by being metabolized by the body, the product is usually a drug. For example, human drugs are regulated by the FDA's Center for Drug Evaluation and Research (CDER), but biological products which include blood and blood products are regulated by FDA's Center for Biologics Evaluation and Research (CBER). And, finally, the FDA's Center for Veterinary Medicine (CVM) regulates products used with animals.

The nomenclature of medical devices is a coding system used to describe medical device categories and to generically identify medical devices and related health products. Product classification and nomenclature in the global healthcare sector is quite complex. Several naming systems for medical devices exist and each is used by a different group of professionals depending on the needs of that particular group, needs such as maintenance, procurement, accounting, stock keeping, regulatory affairs, adverse medical device event reporting, and customs operations (CMDR, DM&D, eCl@ss, GMDN, GPC, HCPCS, MedDRA, NAPCS, NHS eCl@ss, UMDNS, . . . ). There are also on the market different types of labeling systems for devices and products for medical use (e.g. GS1 or HIBC). On other hand, ISBT 128 is intended only for products of human origin.

Supply chain management and optimization has become a priority area for global health systems due to increasing complexity of healthcare supply chains and the availability of IT solutions. Globally, supply chain transformation is becoming a priority area for many healthcare systems who are aiming to control rising costs An UDI is a unique numeric or alphanumeric code, usually in the form of a barcode, that can be displayed in both human readable (plain text) and machine readable (AIDC) form; it identifies a device at the point of distribution and at the point-of-use that consists of two parts: a device identifier (DI) and production identifier(s) (PI). The Device identifier (DI) is a mandatory, fixed portion of a UDI that identifies the specific version or model of a device and the labeler of that device. The production identifier (PI) is a dynamic number that is determined by various data (such as batch number, serial number, expiration date, and date of manufacture).

There are different initiatives throughout the world to develop Unique Device Identifiers (UDI) in each country or region; different countries have developed or are developing their own databases and identification systems for medical devices, such as the FDA GUDID for U.S. and EU-UDI for Europe, for example. These systems are independent of each other and, therefore, keep the data isolated in different databases. They also differ in the fields that define each product and in the way of identifying the labeled products.

In Europe, for example, UDI carrier contains DI+PI in a machine (AICD) and human (HRI) readable representation. In U.S. only AICD is needed. AIDC data carrier is based on ISO standards (bar code, data matrix, RFID) and the data is formatted in a code standard (e.g. GS1, HIBCC). In Europe the AIDC format is favored in case of significant space constraints on the device or packaging; however, the use outside of healthcare facilities requires HRI on the label.

European regulations requirements on generating clinical evidence on medical devices across their entire lifecycle. Europe MDR/IVDR requirements for some devices is "to continuously generate, collect, analyze and assess the clinical data pertaining to a device in order to verify the safety and performance, including the clinical benefits, of the device when used as intended by the manufacturer."

Globally harmonization goes beyond making it easier for manufacturers who have to comply with regulations in many different countries. Using a common approach to product identification provides important downstream benefits for regulators, providers and patients as well. Given that many devices sold around the world are similar if not the same across various countries, the data generated on a device in one part of the world can be relevant for data consumers elsewhere.

Inconsistency in the format used to identify medical devices and the lack of a harmonized nomenclature and structure for medical device identification information, currently result in an inability to compile effective market surveillance information about a medical device or product. Lack of a common unified identifier for a universal medical product identification also makes it possible that a medical device may be referenced distinctively in different countries, which limits the ability to compile data or make comparisons across countries. The invention that is intended to be patented allows for cooperation between the different stakeholders (individuals, organizations, regulators, distributors, etc.) in order to improve the traceability of the products worldwide, create alerts, carry out studies and follow-up on donations, blood transfusions, tissues and organ transplants and other related medicines.

At present there is no known the existence of a system that allows a unified record and a universal identification of biological products of human or animal origin for medical ends in a cross-border way between different countries and systems of codification of products, that could be used from any place in the world to register the deals carried out on these products (like collection/delivery, purchase/sale, change of owner, . . . ), and to be aware of alterations in the conditions of the product along the whole life of the same one from its origin or production up to its use, which could bear the automatic rejection of the product and prevent it or its derivatives from being used in case of some anomaly being detected.

Consistent use of a universal identifier for biological products from human or animals and for medical or veterinary purposes will solve the above problems by providing a common way to refer to a product and enables tracking and reporting unambiguously on the regulatory marketing status of a medical device around the world, as control of biological medicines such as vaccines and blood products, and is essential for making sure the biological medicines that patients receive (humans or animals) are safe and effective. However, the existence of a unified and universal system for the global identification and traceability of products of biological origin is not known, nor is there a unified global register of clinical trials and of organizations that manufacture products of biological origin for medicinal purposes.

On the other hand, as has been mentioned above, there is no known unified global register of individual receivers or clients of biological products for medicinal purposes of any kind (transfusions, transplants, vaccines, etc.). Currently, if an individual receives a blood transfusion in a certain center and a time later it is discovered that the origin donor of the product has suffered cancer and wants to perform a traceability of the recipients of the product or products, the isolation of data between the different centers prevents this in practice, unless the new center belongs to the same organization as the other center and uses the same data management system, perform an automatic and universal traceability of the individuals receiving products of biological origin for medical or veterinary purposes, and it is not possible to identify these recipients in any other center than the one in which the product was used. For example, if an individual resides in a different region or country, currently that individual cannot relate to a universal identification code of a recipient or client of a biological product for medical or veterinary purposes, nor can this information be automatically related to a donation center in case the person is a donor. This produces in practice that, for example, neither the recipient nor the medical staff from another center in a different organization, region or country can receive an automatic alert to perform medical tests and follow-up after any anomaly is detected in a specific product of biological origin as well as automatically excluding the individual to donate during a certain time.

A complete cross-border traceability between different territories is necessary, labeling systems and regulations, including universal traceability from the origin of the biological products (obtention or manufacture), to the batch of the products, their use and vice versa, as well as being able to notify intermediaries that have used material of biological origin in a production process any event that may affect the quality or safety of the product and any other information found after obtaining the material of biological origin related. The principles of risk management for quality (Quality Risk Management, QRM) are, therefore, especially important. In addition, the data necessary for complete traceability must be retained for at least 30 years in some countries.

An example of use of what this invention allows would be the one described below. A regular blood donor dies and, after performing an autopsy, tumor cells or a tumor is detected in the deceased donor. Thanks to the existence of a unified global registry of products of biological origin for medical purposes and of the different related parties, this situation could be alerted automatically to all the related centers, as well as to quarantine all the products that have been manufactured from the previous blood donations from the donor and follow up on the products that have already been used (platelet units, blood units, plasma, manufactured vaccines, etc.) to take appropriate actions, such as monitoring of clients, patients and/or users who have received these products, allowing, on one hand, to study in a transversal and in depth manner these cases to be able to establish additional measures or protocols based on the results obtained, and on the other hand, to study the appearance or not of this type of disease in all the individuals involved.

In conclusion, and as a reference to the current state of the art, it should be noted that, although different regulations, types of user registration systems and registration and labeling of medical devices and products are known on the market, at least on the part of the applicant, the existence of any one with technical and constitutive characteristics similar to those presented by the invention that is asserted here is unknown.

SUMMARY

The invention, as expressed in the statement of this descriptive report, refers to a unified global registration procedure for all territories of products of biological origin for medicinal purposes in humans or other living beings (such as blood, its components and its derivatives such as plasma-derived medicinal products; other tissues such as nerves and blood vessels; other cells such as ovules and master cell lines; organs; others products of biological origin such as insulins, . . . ), of the distinctive related parties (individuals origin and/or destination of the products such as donors, recipients, clients, users or patients both humans or other types such as animals; other parties involved in the chain of obtaining, manufacturing, processing, storage, transportation and use of these products, clinical interventions, . . . ) and for the universal identification of both any product and any of the parties related to it (individuals and entities such as organizations, companies, donation and transfusion centers, laboratories, clinics, hospitals, personnel, . . . ), which presents advantages and characteristics, which will be described in detail later, which infer an improvement of the current state of technique.

Products of biological origin for medical purposes have in common that they come from living beings or use in their manufacture materials that come from living organisms, and include, among others, blood products (transfusions of red blood cells, platelets, . . . ), tissues and organs for transplants, medicines of biological origin such as vaccines, cells, advanced therapies such as tissue engineering and other biological products such as biotechnological medicines (erythropoietins, insulins, . . . ).

The object of the present invention falls, specifically, in a procedure whose purpose is to achieve the unification of the registration and identification of the products of biological origin (obtained from donors or from other sources) and of the different parties related to the obtention and use of the these (entities, human or other individuals, . . . ) in order to facilitate the access and monitoring of the data in the entire chain of collection, production, supply and utilization of the products of biological origin (obtained from donations or from other sources) for medicinal purposes in humans or other living beings, in a universal manner, from the origin (human or of another living being) until the final use of the product in humans or in other living beings, to certify anywhere, and in a universal manner, the origin, the destination or recipient, as well as the intermediaries and the quality control of the products, in order to:

facilitate, on one hand, the exchange of information related to the products (center of origin or manufacturing, storage, distribution, receiving center, clinical intervention, . . . ) and, on the other hand, the unification of the health data of the individuals that are the origin or the destination of the biological products for medicinal purposes (medical or veterinary);

improve and facilitate the identification of individuals in a universal manner such as donors, recipients, users, clients and patients, humans or other types;

facilitate, in a universal manner, the identification and access to the data of the products along the chain of collection, production, distribution, supply, utilization, etc., in a unified and universal way, from their origin (human or other types such as animals) until their final use in humans or other living beings;

allow transverse traceability of products of biological origin between different territories, related parties and systems;

record the transactions made with the product throughout the production, supply and utilization chain by all the parties involved;

certify in any place and universally both the origin of the product and all intermediaries related to it;

certify, control and track the quality of the products;

save financial resources; and increase the safety of donations, transfusions and transplants of any kind as well as other types of products of biological origin.

This procedure means a particular method to carry out the steps of both phases for the unified registration and for the universal identification of products of biological origin for medicinal purposes; this method consists of setting up, by centers responsible for the obtention, generation or manufacture of the products (donation centers, hospitals, laboratories . . . ) and/or by the centers responsible for the use of the products (hospitals, clinics, . . . ), through a software application running in an electronic device (computer, mobile, tablet, . . . ) with network connection to a computer system, the following:

a global and unique data storage vault (B102) for each of the data objects for the parties and entities (B103), as an individual (human or other types), product (such as units of plasma or red blood cells, immunoglobulins, vaccines, organs or tissues), or other parties (collection center, manufacturer, clinical trial, clinical intervention . . . ), stored in a database (B101) accessible through a (main) computer system (B100), e.g. in JSON format via REST API or gRPC (B05, B06), among others;

one or more regional data vaults (B12, B22) associated with the global storage vault (B102), each regional vault containing data from one or more local computer systems (B1, B2) in each geographical region or specific territory (T1, T2) for distinct data objects (B14, B24) and each regional vault store the data in different databases (B11, B21) accessible through a regional computer system (B10, B20), e.g. via REST API (Representational State Transfer Application Programming Interface), GraphQL (Graph Query Language) or gRPC (Google's Remote Procedure Call), among other possible, for compliance with different regulations (identification of products, storage of personal data, . . . );

one or more profiles for the data objects (in JSON format, among others possible) associated with each global vault (B106, B108) or regional vault (B16, B18, B26, B28) which contain public information (B106, B16, B26), e.g. blood group in the case of an individual and expiration date in the case of a product, or private data (B108, B18, B28) for use by the individual and/or the parties related to the product and authorized to access said private information, such as relevant information on the product (temperature control, tests performed, . . . ) or on the individual (diseases or relevant health disorders, clinical interventions, relevant medical or health treatments, prescription or recent consumption of medication, allergies, relevant medical reports, analytical tests, . . . );

a unique and non-transferable internal identifier (e.g. an UUID using version 4, among other possible) to identify univocally in the system both each generated profile and regional vault (B107, B109 B13, B15, B17, B19, B23, B25, B27, B29), internally relating the information stored in these different profiles and regional vaults with the data object generated for a determined individual or product in the global storage vault (B113);

a unique and non-transferable public identifier associated with the data object in the global vault (B104) to uniquely identify the parties (individual, product, center, . . . ) as data objects (B103) and access public stored data, for example in an URN (Uniform Resource Name) with an UUID (Universally Unique Identifier) in v4 format (hexadecimal random numbers) generated by a software application using random bytes (e.g. urn:public:product:uuid:38735183-d078-494d-*b*3b5-fbfebaccadf6), among other possible;

a unique and non-transferable private identifier associated with the global vault (B105) for access by each related party to the data to which it has access permissions in the data object (B103), allowing anonymization and privacy of personal or medical data related to the individual and of private data related to the product, for example in an URN with an UUID v4 (hexadecimal) generated by a software application using random bytes (urn:private:product:uuid:38735183-d078-494d-b3b5-fbfebaccadf6), among other possible; and a non-transferable public identification code (B118) that contains at least one field for storing the public identifier (B114), e.g. using JSON data (among other possible), and, optionally, other fields for storing the private identifier (B115) and/or other data (B116) such as the blood group of an individual or product, or production date, batch number and/or expiration of a product.

The regional data vaults (B12, B22) and the associated profiles (B16, B18, B26, B28) relate the information stored in a data object (B103) for an individual, product or other related parties in the (main) computer system (B100) with the different systems of databases and existing identification systems (B110) in distinct local computer systems of different territories (B1, B2), such as personal data and profiles with medical data in the case of an individual, or production and storage data in the case of a product (B16, B18, B26, B28), by using different internal identifiers (B15, B17, B19, B25, B27, B29).

The data related with each data object in the global data storage vault (B103), the data related with it in the regional data vaults (B14, B24), the profiles generated in the data object (B106, B108) and the public identifier (B104) are associated with a unique and non-transferable identification code (B118) that allows access to public data and, optionally, to other information by including the necessary data in the identification code. These data are deposited and stored in the database (B101) of a (main) computer system (B100) accessible by the different related parties (individuals, producers, intermediaries, . . . ) based on the access permissions in each case (B07, B08).

The identification code (B118) contains a set of data defined in fields that identify it as unique and that can also be stored in the system database (B101) and includes, at least, the public identifier and, optionally, other data such as blood group, prescribed medication and contacts for emergencies in the case of an individual (B116).

BRIEF DESCRIPTION OF THE DRAWINGS

To complement the description that is being made and in order to insure a better understanding of the characteristics of the invention, the present descriptive report is accompanied, as an integral part thereof, by a plan in which, with an illustrative and non-limiting manner, the following is shown.

DETAILED DESCRIPTION OF THE INVENTION

Figure 1:
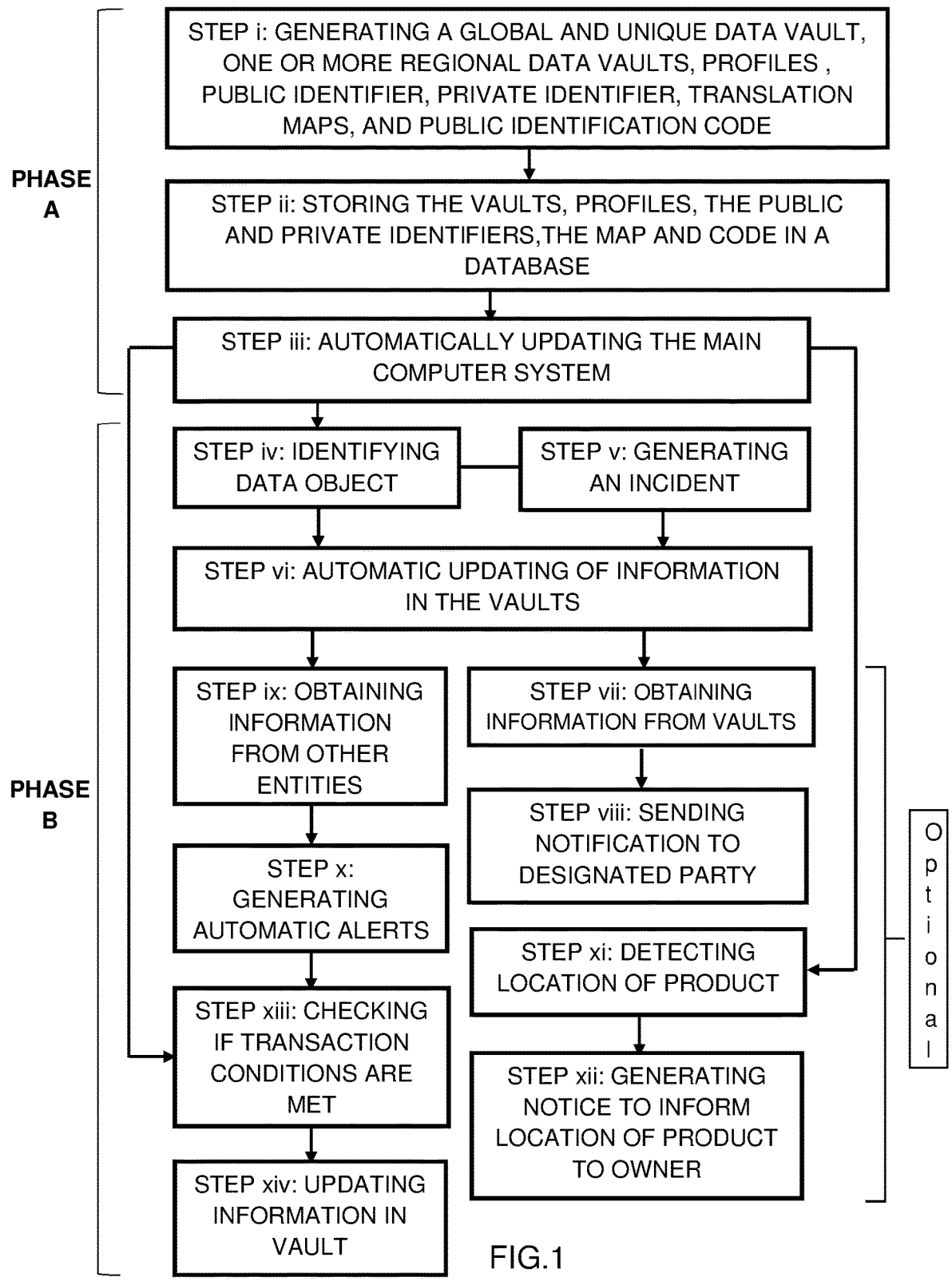
FIG. 1 shows, by means of a block diagram, the flow diagram of the operational steps for the method of the invention.
Figure 2:
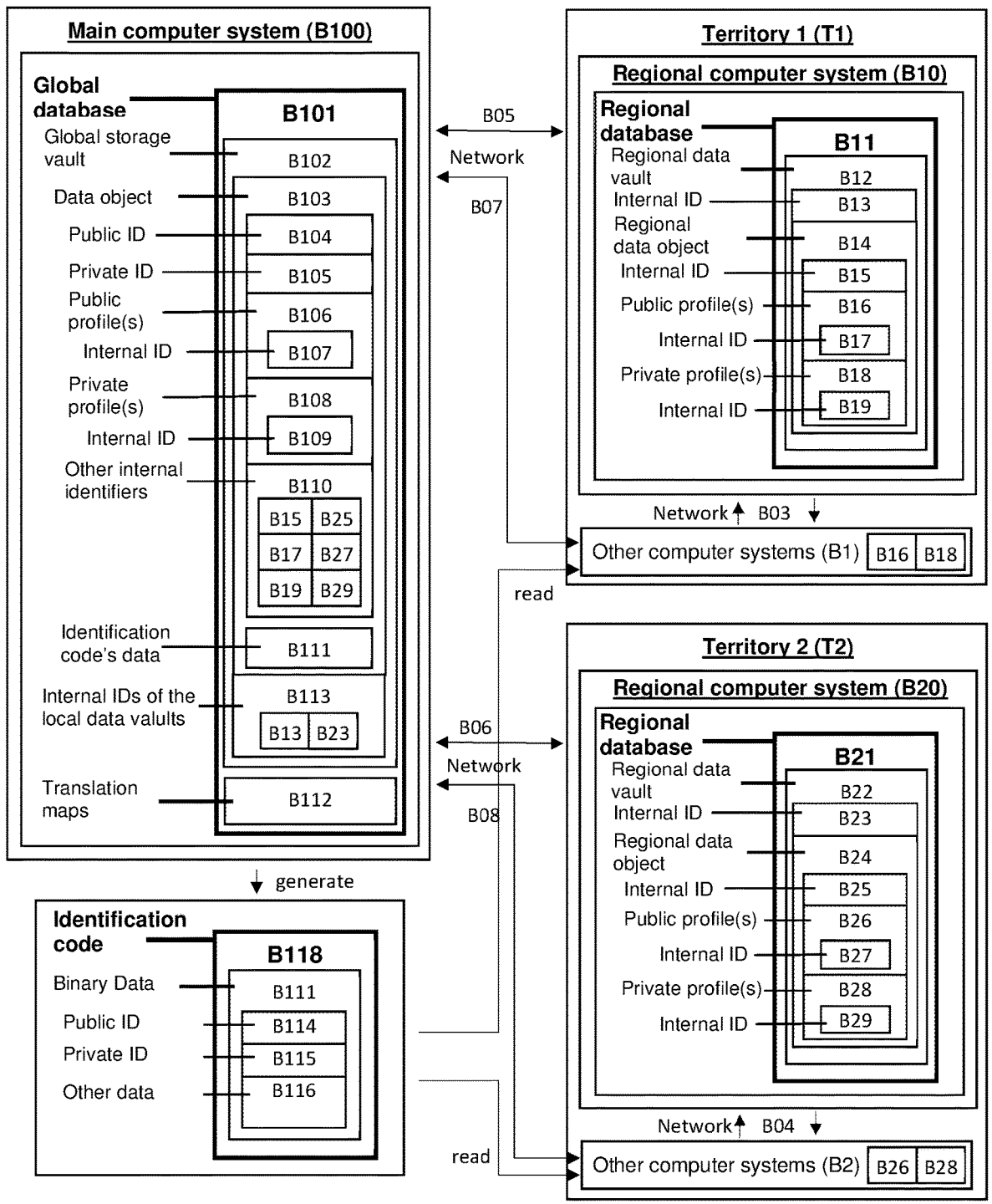
FIG. 2 shows the binary data communication and storage of the information according to the invention.
Figure 3:
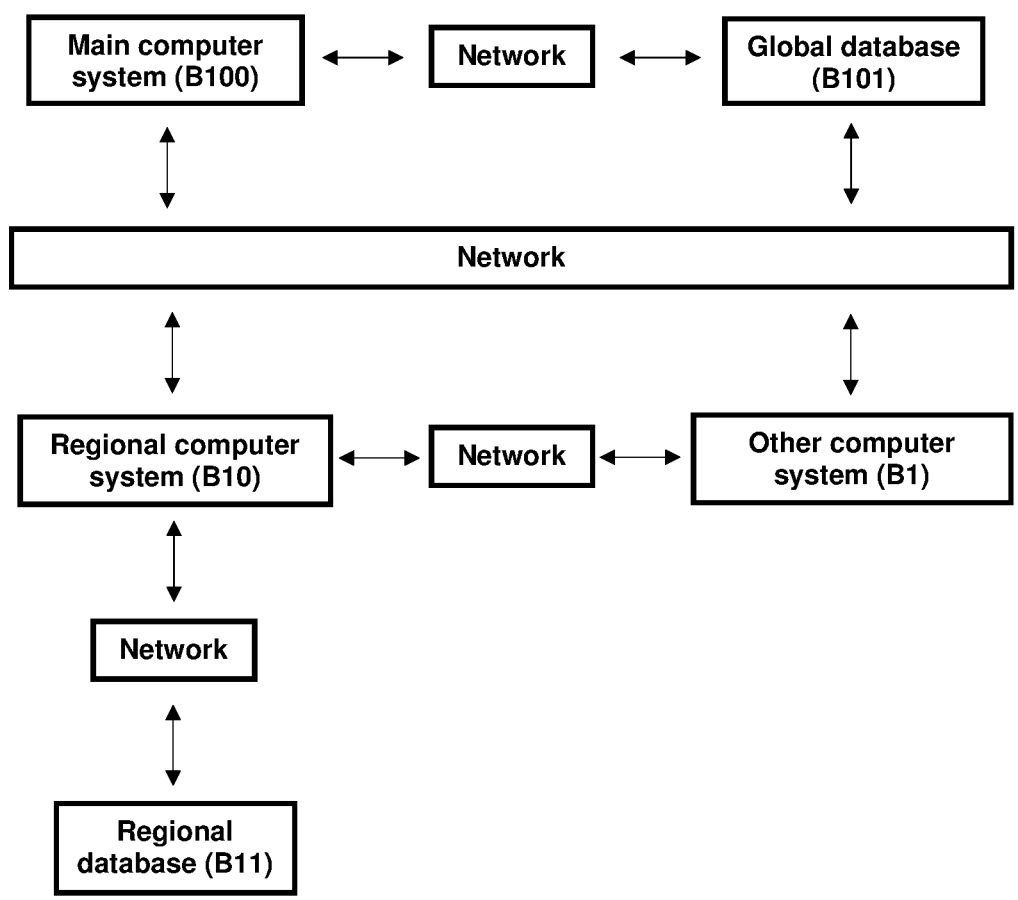
FIG. 3 shows the network connection schema according to the invention.

The procedure for the unified global registry and universal identification of products of biological origin for medicinal purposes in humans or other animals and of the different related parties proposed by the invention is configured as a novelty within its field of application, since according to its implementation by the method of the invention the above-mentioned objectives are satisfactorily achieved, its characteristic details being conveniently collected in the final claims that accompany the present descriptive report.

As explained above, products of biological origin for medicinal purposes include, among others, blood products (transfusions of red blood cells, platelets, plasma, . . . ); medicines of biological origin such as vaccines; cells, tissues and organs for transplants; advanced therapies such as tissue engineering; and other products and biological medicines.

Specifically, what this invention proposes, is the development of a global process for the registration and for the universal identification of products of biological origin for medicinal purposes and of the different related parties such as individuals (donors, recipients, clients, users, patients), origins of products or biological materials (human, animal, cell lines, . . . ), entities related to the obtention, manufacturing, processing, supplying and utilization of products, clinical trials and clinical interventions or treatments in which products are used, whose purpose is to achieve the unification, in all territories and for any existing software solution, of the registration and identification system of these products and of the related parties, from the origin (human or another living being) to its final use in humans or other living beings, to facilitate the exchange of information of the products and between the different related parties as well as the traceability and cooperation between the different participants in the collection, production, storage, transport, processing, distribution and utilization phases.

The communication of binary data between the local computer systems of the authorized centers (B1, B2) and the computer systems of the invention (B100, B10, B20) will be carried out in a secure manner (B03, B04, B05, B06, B07, B08) by using Secure Sockets Layer (SSL) and/or Virtual Private Networks (VPN), among others possible.

The unified global registry and the universal identifier that the invention proposes aim, on one hand, to identify the products, individuals and to each of the parties related to them in a global and univocal way and, on the other hand, to obtain and store the relevant information of all of them. In the case of products, it serves to identify them and to record the relevant events and transactions that take place with the products throughout the production and/or supply chain; in the case of individuals (such as donors, clients, users, patients), it serves to identify them in a global way and to follow up on their clinical history as well as to collect relevant medical or health information; in the case of other biological origins such as cell lines, it serves for identification (which may correspond to a lot number) and the recording of variations in production (growth conditions, compounds used to stabilize the protein, manufacturing conditions, . . . ); in the case of clinical interventions in which products of biological origin are used, it serves to relate the products, the center that performs the clinical intervention and the individual that receives the product; in the case of collection, manufacturing, storage, supply and utilization entities, it serves to identify each one as well as authorized devices and personnel with a network connection to the computer system.

The method proposed by the invention is to unify and facilitate the monitoring of the whole chain of obtaining, producing and controlling the quality of the products, the supply and utilization chain, as well as retrieving information from these parts and the products, such as their origin, their destination, the manufacturer, the control of the storage conditions such as the cold chain, its utilization in a recipient, possible complications or adverse reactions, in order to facilitate and achieve a global monitoring of origin to recipient and of recipient to origin to achieve universal traceability in both directions.

The public identification code (B118) serves to identify a product or other related parties such as a collection or manufacturing center, a donor, a cell line, a clinical, hospital or veterinary center, a recipient, a user or a patient and it preferably has two types of information. A first type, of public information (open accessibility) such as the public identifier (B104) and other information such as blood group, date, place of origin, use of the product, expiration date and quality control, variable in each case (B116). A second type of information will be accessible only from centers and personnel with the required permissions to decipher this information (e.g. health data of the individual, analytical data, production reports, etc.).

For this, said method essentially comprises the following:
setting up, through a global database (B101) and regional databases for each territory (B11, B21) accessible by the different centers and authorized users through a computer system for each database (B100, B10, B20), of:
a global and unique data storage vault (B102) which is a defined collection of data in one logical container in the global database (B101), to store data objects of the parties and entities in the global database (B103) and accessible through a main computer system (B100), e.g. via REST API or gRPC among others (B05, B06, B07, B08), carried out after a voluntary data object storing request made by an individual or by one of the related parties through a software application or service running in a local computer system and/or in an electronic device (B1, B2) such as a server, computer, or tablet with a network connection to the computer system via REST API or gRPC among other possible (B05, B06);
one or more regional data vaults (B12, B22) associated with the global storage vault through internal identifiers (B113, B13, B23), each regional vault containing data from one or more local computer systems in each geographical region or specific territory (B16, B18, B26, B28) and each regional vault store the data in different databases (B11, B21) accessible through a regional computer system (B10, B20), e.g. via REST API or gRPC among others, for example for compliance with different regulations such as identification of products and/or data residency; and one or several profiles for the data objects (B106, B108, B16, B18, B26, B28), e.g. in JSON format among others possible, and associated with each data vault generated in the system, and that contains:

public information of the product accessible to any user, and private information that is managed and shared by the different related parties;

a unique and non-transferable public identifier associated with the data object in the global vault (B104) and to identify the type of data it refers to (individual, product, entity, clinical intervention, . . . ), for accessing public data stored in the data vaults and/or associated profiles, e.g. by using an UUID version 4 in hexadecimal and URN format (such as urn:public:product:uuid: 38735183-d078-494d-b3b5-fbfebac-cadf6), among other possible;

a unique and non-transferable private identifier associated with the global data storage vault (B105) and to identify the type of data it refers to (individual, product, entity, clinical intervention, . . . ) for accessing both public and private stored data by authorized entities and personnel in each case, e.g. by using an UUID version 4 in hexadecimal and URN format (such as urn:pulic:product:uuid:38735183-d078-494d-b3b5-fbfebaccadf6), among other possible;

one or several alphanumeric-hexadecimal translation maps stored in the global database (B112) and associated with the public identifier and the private identifier;

a unique public identification code (B118) containing at least one field for storing the public identifier (B114) generated from the non-transferable public identifier with the hexadecimal format and a concrete alphanumeric-hexadecimal translation map, and optionally other fields for storing the private identifier and/or other data;

automatic update by the system of the data storage vault and/or profile data with relevant events and the date on which they occurred, related either to products, individuals or others (detection of a disease or prescription of a treatment in an individual, transactions or changes in the temperature conditions of a product, utilization of a product in a clinical intervention, . . . ); and identification of the data object stored in the data storage vault and the type of data stored (product, individual, clinical intervention, entity, . . . ) by reading the public identification code (B118), for example through a camera or NFC sensor installed in an electronic device that runs a software application executed by a public user or by an entity and its authorized personnel or by a software service running in a computer system (B1, B2), to decode the binary data of the code for access to the information of the information and the profiles of the data object stored in the data vault; generation, registration and communication of an incident if there is an impediment, carried out by the main computer system and/or by a software application running in an electronic device (e.g. a server, computer, tablet); and automatic updating of the information in the vault and in the profiles of a data object in the database accessible by the different parties and users, carried out by the main computer system (e.g. via REST API or gRPC, among others).

Should be understood as relevant events those that may affect the safety of the product, any of the procedures or processes or the individuals involved, such as diseases, medications or treatments of an individual and variations in the temperature of conservation of a product, elapsed time without receiving information about the product, expiration of the product due to expiration or for other reasons. The capture of these events will be done automatically by the system or by means of authorized entities and users.

Optionally, it also contemplates:

Obtaining information on a collection, donation, manufacture, utilization or clinical intervention process (such as date, time, type of product, origin, destination, among others), for example via REST API or gRPC (among others), store this information in the corresponding vaults and profiles and, optionally, notify the owner or entity responsible for the process (right analytical result, for example) for example via email, SMS, or push notification to a software application.

Obtaining relevant information from other entities (e.g. from medical centers, health authorities, among others via REST API or gRPC, among others), and incorporate it into the stored vaults and profiles, either for public access to said information or for private access from authorized entities and personnel.

Obtaining data from the product itself using telemetry devices incorporated in the product or devices to which the product is associated (such as geolocation, temperature and other variables), store them in the database (e.g. via REST API) and update product information when results are available.

Generate automatic alerts (e.g. via email, SMS, push notification to a software application or by a logging service) when certain conditions are met, such as variation in temperature, near expiration or product wastage for a specific cause, carried out by the computer system (e.g. invalid product, expired date, among other possible).

Send a global alarm to all parties involved and related to the process after detecting a serious illness in a donor or a serious anomaly in any of the related processes (collection, production, supply, utilization) to initiate protocols and check donations or related products that may be affected (e.g. via email, SMS, push notification to a software application, by a logging service, among others), carried out by the computer system.

Store in the product profiles stored in the global data vault and/or in the generated identification code distinct universal product code identifiers of one or more countries (GUDID, EU-UDI, . . . ) and one or more product labeling systems (ISBT 128, GS1, HIBC, . . . ), carried out after a voluntary data object storing request made by an individual or by one of the related parties through a software application or service running in a local computer system and/or in an electronic device such as a server, computer, or tablet with a network connection to the main computer system.

Associate the product with one or more links to web addresses in the identification code of the product generated and/or in the public information of the product stored in the data vault, so that any user can consult commercial information or public access data related to the product (for example through a camera or NFC sensor installed in an electronic device that runs a software application).

Going into more detail it should be noted that, the unified code for the identification of a biologic originated product generated according to the procedure of the invention will be UDI compatible by containing both UDI-DI and UDI-PI in the additional data (B116) and will be deposited or printed on the product itself univocally and non-transferable, by means of a human readable alphanumeric code (HRI) and a machine readable code (MRI) to be read automatically from an electronic device and carried out preferably on a NFC tag without ruling out other options (such as a QR code, for example), and includes a series of data that identify and distinguish it as unique.

The identification code for the products and for the other related parties, in addition to containing the public identifier (B114) that allows access to public data stored in the system, may optionally contain the private identifier (B115) for access to private information (which can only be accessed and deciphered by an authorized device and personnel), and may also include information to be legible and consulted by any user such as UDI codes in one or more territories or jurisdictions, production date, blood group, expiration, etc. (B116). Optionally, said identification code, once generated, can also be stored in the global database of the main computer system accessible by the different parties and/or users (producer or manufacturer, intermediaries, customers, recipients, consumers, ... ) via REST API or gRPC among other possible.

According to the above, the method of the procedure will allow generating, global public and private identifiers, unique and non-transferable, as well as the unique identification codes of:
- products of biological origin;
- individuals (human or other types) as donors, clients, users and patients;
- cellular production lines;
- entities such as companies, organizations, donation centers, medical centers, clinics, hospitals, laboratories, as well as related personnel and devices to access the system;
- clinical trials, clinical interventions and treatments whether medical in humans or veterinary in animals.

It is remarkable that, on one hand, the identification code for an individual may contain certain health and medical information for emergencies that the user has approved for publicly sharing such as blood group, prescribed medication, allergies and contacts for emergencies. On the other hand, and as security measures, the computer system (B100) additionally can notify the individuals and/or their contacts when the information of the identification code is read and the user and/or the device, entity and personnel that makes the reading will be identified (e.g. via email, SMS, push notification to software application, among others). Furthermore, if access to private medical information is required by an entity and/or personnel to which the individual has not granted permission, the access permissions will be requested to the individual and/or to the contacts established for such case through a notification.

Going into more details, the public identifier will be composed of a set of alphanumeric characters called "error-free" that cannot be confused with each other due to wear, dirt or bad printing of them, in order to avoid errors in the identification. This set will consist of only 16 characters that form an alphanumeric-hexadecimal map translation and that is stored in the system, formed by but not limited to "ABEHKMNOSWXYZ349", that allows the identification of a specific letter even though only a part of said letter can be read. Said identifier will preferably have a length of 32 characters, so that the number of possible public identifiers using this format is 16 raised to 32, or about 3.4×10 raised to 38. Each of the characters will have an equivalence with a hexadecimal number using the defined translation map, and this equivalence may vary with each version of the public identifier that is implemented. On the other hand, said product identifier may contain a series of characters that allow determining the version of the translation map used and also one or more redundancy characters to perform the automatic error detection and correction by the system when the identifier is read.

The direct translation of alphanumeric character to hexadecimal number is carried out by the computer system (B100) using the character translation map stored in the global database (B112). The public identifier (B104) preferably contains an UUID in v4 format (random Universally Unique Identifier), without discarding others.

On the other hand, the creation of translation maps of alphanumeric characters to hexadecimal numbers adds an extra layer of security to avoid that the generation system of public identifiers can be discovered and makes it possible to change the alphanumeric coding of the public identifier simply by assigning a new map translation of alphanumeric characters, without the need to make other modifications in the identification system.

It should be noted that each of the data profiles associated with data objects in the global storage vault (B106, B108) are generated either by an authorized entity and personnel that performs the registration or creation of the data object in the global storage vault or by any of the other authorized related parties for data storage, through a software application running in an electronic device (e.g. server, computer, tablet) and/or computer system with network connection to the main computer system of the invention (B5, B6, B7, B8) via REST API or gRPC, among other possible.

With all the above, thanks to the identification code generated, the identification of the product or any of the other related parties can be made by a computer equipment or electronic device conveniently installed for this purpose and, through the identification data of the code (B118) and the corresponding access permissions in the private profiles (B108, B18, B28), to access to the data of the vaults and profiles stored in the computer system (B100) to which the access permission has been granted in each case.

In case of existence of any impediment to generate the registration of a data object or profile in a data vault, access to specific data, make a transaction (purchase/sale, sending/receiving, ... ) or for the utilization of a product (absence of analytical, breakage of the cold chain, incompatibility, ... ), the computer system (B100) can send a notification and a software application installed with network connection with the computer system can generate an alarm to alert of this circumstance to the related parties and to the corresponding personnel.

The generated identification code (B118) also allows the content of the information it incorporates to be varied, so if the information of the data object and their associated profiles in the database accessible by the different authorized parties changes (date storage or fractionation, delivery/collection, etc.), the identification code changes dynamically.

Optionally, the computer system (B100) will be able to capture information from other computer systems (e.g. via REST API or gRPC, among others) and associate this information to the data objects and their profiles in the data vaults such as analysis and other data of the production and/or supply chain, or data from telemetry devices incorporated in the product or from other devices to which the product is associated (such as geolocation and/or temperature) and store them in the database accessible by the different parties. The computer system may incorporate all or part of said additional information that will be introduced into the data object and the corresponding associated data profile, either automatically or selectively through a software or application running in an electronic device with a network connection to the computer system.

In addition, the computer system is able to send a notification to a software application in an electronic device of an individual (donor, user, client, recipient, patient) and/or to a computer system of the entity (s) and/or to a software application of authorized personnel when there are updates on the status of any type of information with which it is related (analytical received, close expiration, etc.).

Optionally, the computer system (B100) may alert related parties and designated personnel to receive notices by receiving relevant information from authorized entities/centers or from telemetry devices (e.g. in case of detection of a relevant disease in a donor or breakage of the cold chain) and incorporate said information into the corresponding data object and profile in the data vault.

The computer system (B100) can also automatically detect the location of the products (for example via REST API) and inform the related entities and designated personnel to receive this information by generating notifications (e.g. by email, SMS, push notifications to a software application or through a logging service, among others), as well as indicate an estimated time of arrival of a product, for example for the performance of an organ transplant or a blood transfusion. The detection of the product is made by the computer system through geolocation means that incorporate the product itself such as those included in its packaging or through electronic devices to which the product is associated, such as a SIM card through a mobile phone or other geolocation device with network connection with the computer system, provided by the service and/or personnel carrying out the transport.

In case of detection by the system of any discordance or absence of certain data entered, stored, collected or received, the system may assess the situation and warn the related parties (collector, producer, transport, recipient, etc.), and mark the related data as erroneous or pending verification. For example, if the registration of a product is made from a universal donor identifier and the blood group associated with the donor does not coincide with the result of the blood test, the system will warn of this situation and mark the product as pending of verification and not suitable for use. Likewise, the rest of the bags of blood collected on the same day by the same donation center or analyzed on the same day by the same laboratory can be marked automatically to request a verification of the rest of the products that may be involved.

The discreet method of the procedure for the unified global registry and universal identification of products of biological origin for medicinal purposes in humans or other animals and of the different related parties consists of an object of unknown characteristics thus far for the purpose for which it is intended, reasons which, combined with its practical utility, provide it with sufficient grounds to obtain the privilege of its exclusivity which is required.

In view of the described figure, and in accordance with the numeration adopted therein, it can be seen how the procedure essentially comprises of the following phases and steps:

In a first phase (A) for the unified global registry of products of biological origin for medicinal purposes and of the different related parties comprises: i) generating a) a global and unique data vault in a global database accessible by the different parties through a main computer system (e.g. via REST API or gRPC) to store data objects for each of the parties (e.g. in JSON format, among others possible), carried out after a voluntary data object storing request made by an individual or by one of the related parties through a software application or service running in a local computer system and/or in an electronic device such as a server, computer, or tablet with a network connection to the main computer system; b) one or several regional data vaults associated with the global vault through internal identifiers and containing data stored in each specific geographic region or territory; c) one or several profiles associated with each data object generated that store public information accessible to any user and private information that is managed and shared by the different related parties; d) a unique and non-transferable public identifier associated with the data object in the global vault, for example in an URN with an UUID v4 (hexadecimal) generated by a software application using random bytes; e) a unique and non-transferable private identifier associated with the global data vault, for example in an URN with an UUID v4 (hexadecimal) generated by a software application using random bytes; f) one or several alphanumeric-hexadecimal translation maps, stored in the global database, and associated with the public identifier and with the private identifier, formed by a set of error-free characters such as ABEHKMNOSWXYZ349 that allow the identification of a specific letter even though only a part of said letter can be read; g) a unique public identification code containing at least one field for storing the public identifier generated from the non-transferable public identifier with the hexadecimal format and a concrete alphanumeric-hexadecimal translation map, and optionally other fields for storing the private identifier and/or other data, to which the public identifier, the data object in the global data vault and the rest of the generated regional data objects and profiles in the regional vaults are associated; and ii) storing the generated vaults, data objects and profiles, the private identifier, the public identifier, the translation map and the identification code in a database accessible by the different parties through a main computer system (e.g. via REST API) according to their access rights to the data; iii) automatically updating by the main computer system of specific data objects and profiles with relevant events and the date on which they occurred (clinical interventions, diseases, donations, allergies, adverse reactions, . . . ) after capturing or obtaining this information from other computer systems and/or electronic devices (e.g. via REST API or gRPC, among others).

Once the first phase (A) of the method is realized, the second phase (B) for universal identification of products of biological origin for medicinal purposes and of the different related parties can be carried out. Phase (B) comprises: iv) identification of the data object stored in the data storage vault and the type of data stored (e.g. product, individual, clinical intervention, entity) by reading the public identification code, for example through a camera or NFC sensor installed in an electronic device that runs a software application executed by a public user or by an entity and its authorized personnel or by a software service running in a computer system, to decode the binary data of the code for access to the information and the profiles of the data object stored in the data vault, based on the access permissions that are active when accessing the data; v) generating, registering, and automatically communicating an incident in case of existence of any impediment when making the identification, accessing the data, making the registration of new information, when a verification is required or when certain previously established conditions are met (e.g. variations in the temperature, close expiration, rejection of the product for some reason), carried out by the main computer system and/or by a software application running in an electronic device such as a server, computer or tablet (e.g. via email, SMS, push notification to a software application, by a logging service, among others); vi) automatically updating of the information in the vaults and profiles stored in the database accessible by the different parties with data on the process of obtaining, manufacturing, supplying and/or using (e.g. lot number, result of analysis performed, shipping/reception transactions, utilization in a clinical intervention, data of the individuals), carried out by the main computer system (e.g. via API REST or gRPC, among others).

In addition, optionally, the method of the procedure contemplates, in this use phase (B): vii) automatically obtaining information from a collection, donation, supply, utilization or clinical intervention process and store this information in the corresponding vaults and profiles in the global database, carried out by the main computer system (e.g. via API REST or gRPC, among others); and viii) sending a notification to the related and/or designated parties when the data collected is available for consultation, carried out by the main computer system (e.g. via email, SMS, push notification to a software application, among others).

Optionally, the method also contemplates the incorporation of one or several of the following stages in this phase (B): ix) obtaining relevant information from other entities (e.g. collection of reports, breakage of the cold chain) and automatically incorporate this information into the data object and profiles stored in the global or local vaults, and notify of it to related parties and designated personnel, carried out by the main computer system or by one or several regional computer systems (e.g. via API REST and email, SMS, push notification to a software application, among others); x) generating automatic alerts when it is detected that certain conditions are met (e.g. close expiration, expiration of a product, detection of anomaly), to initiate protocols, request verification or validation of other data or related products that may be affected and incorporate the information to the corresponding data vaults and profiles of a data object, carried out by the main computer system or by one or several regional computer systems (e.g. via API REST and email, SMS, push notification to a software application, logging service, among others); xi) detecting and registering the location of a product through geolocation incorporated in it or through electronic devices to which it is associated (e.g. SIM card by mobile phone, geolocation device), carried out by the main computer system, by one or several regional computer systems or by a software application running in an electronic device (e.g. via API REST); xii) generating a notice and inform of the location of a product to the owner and/or to the destination, as well as the expected delivery or arrival time of the product, carried out by the main computer system or by one or several regional computer systems (e.g. via API REST and email, SMS, push notification to a software application, among others).

Finally, if a new information is generated in the vaults when a transaction is made (sending/receiving, buying/selling, utilization in a clinical intervention, etc.), the procedure optionally contemplates in this use phase (B): xiii) checking that the conditions to carry out the transaction are met and notify the parties (e.g. valid or compatible product, user authorized to write data in the database), carried out automatically by the main computer system after a request received (e.g. via REST API or gRPC, among others); and xiv) updating the information of the data object in the corresponding vaults and profiles with the result of the transaction made, carried out by the main computer system after a response received from the global database (e.g. via REST API or gRPC, among other possible).

In a preferred embodiment, the procedure generates global public and private identifiers, unique and non-transferable, as well as the unique identification codes of:
products of biological origin;
individuals (human or other types) as donors, clients, users and patients;
cellular production lines;
entities such as companies, organizations, donation centers, medical centers, clinics, hospitals, laboratories, as well as related personnel and devices;
clinical trials, clinical interventions and treatments, whether medical in humans or veterinary in animals.

In a preferred embodiment the identification code is deposited in a device that contains a unique identifier such as an NFC tag or similar (e.g. RFID tag) that identifies univocally the device, carried out by a software running in an electronic device configured for that;

In another preferred embodiment, the identification code is deposited in a QR code or similar (e.g. other types of matrix barcodes) that can be alternatively displayed in the screen of an electronic device or printed and associated to parties such as individuals (recipients, clients, users, patients), products and/or origins of products or biological materials, carried out by a software running in an electronic device configured for that;

In a preferred embodiment the identification code contains two types of information such public and private information from the public and private profile(s) of the data object stored in the global database and/or in the regional databases and related with the data object; the permissions are controlled by the main computer system and/or by the regional computer system(s) where the data is requested; the private information can be additionally encrypted in the identification code and in the database and only accessible by the authorized entities and personnel through an encryption key (using a symmetric or an asymmetric encryption key) which is required to decrypt the data for access the private information.

In a preferred embodiment, the identifier of the individuals (donors, recipients, customers, users, patients) is made by using the unified donor identifier as a means of universal identification and for the traceability of individuals in both directions (from origin to destination and from destination to origin).

In a preferred embodiment, the public identifier and the private identifier are generated using an URN format that allows to identify the type of data it refers to (e.g. urn:private:product:uuid:38735183-d078-494d-b3b5-fbfebaccadf6).

In a preferred embodiment, the public identifier and the private identifier are generated in using an UUID in v4 format formed by 32 hexadecimal characters (e.g. 38735183-d078-494d-b3b5-fbfebaccadf6), additionally, the UUID of the public identifier (32 hexadecimal characters) can be converted to an UDI-DI compatible identifier (e.g. in case of products whose are medical devices) both to Base 64 or to Base 58 to fit the maximum length requirements in different regulations (e.g. 23 alphanumeric characters in the USA excluding the check control characters, 25 characters in Europe including the check control characters).

In a preferred embodiment of the invention, the data communication between the local computer systems of the authorized centers, the electronic devices and the global and regional computer systems is carried out in a secure manner by using Secure Sockets Layer (SSL) and/or Virtual Private Networks (VPN), without excluding other options.

As the attributes of the presented invention have been sufficiently described, as well as how to put it into practice, it is not considered necessary to make a more extensive explanation so that any expert in the matter understands its scope and the advantages that derive from it, clarifying that, within its essence, it may be put into practice in other ways of implementation that differ in detail from the application thereof indicated by way of example, and which will also reach the protection that is sought, provided that it is not altered, changed or modified in its fundamental principle.

What is claimed is:

1. A computer implemented method for a procedure of unified global registry and universal identification of products of biological origin for medicinal purposes in humans or other animals and of the different related parties, the method comprising:
    a first phase (A) comprising:
        generating a global and unique data vault in a global database accessible by the different parties through a main computer system to store data objects for each of the parties, carried out after a voluntary data object storing request made by an individual or by one of the related parties through a software application or service running in a local computer system and/or in an electronic device with a network connection to the main computer system, with one or several regional data vaults associated to the global vault through internal identifiers and containing data stored in each specific geographic region or territory, having one or several data profiles associated with each data object generated that store public information accessible to any user and private information that is managed and shared by the different related parties;
        generating a unique and non-transferable public identifier associated with the data object in the global vault by a software application using random bytes in hexadecimal format;
        generating a unique and non-transferable private identifier associated with the global data vault by a software application using random bytes in hexadecimal format, having one or several alphanumeric-hexadecimal translation maps, stored in the global database, and associated with the public identifier and with the private identifier, formed by a set of error-free characters including "ABEHKMNO-SWXYZ349" that allow the identification of a specific letter even though only a part of said letter can be read;
        generating a unique public identification code containing at least one field for storing the public identifier generated from the non-transferable hexadecimal public identifier and a concrete alphanumeric-hexadecimal translation map, and optionally other fields for storing the private identifier and/or other data, to which the public identifier, the data object in the global data vault and the rest of the generated regional data objects and profiles in the regional vaults are associated, the unique public identification code having two types of information, the first type including public information that has open accessibility and a second type of information that is accessible only by others that have required permissions to decipher the second type of information;
        storing the generated vaults, data objects and profiles, the private identifier, the public identifier, the translation map and the identification code in a database accessible by the different parties through a computer system according to their access rights to the data; and
        automatically updating by the system of the data storage vault and/or profile data with relevant events and the date on which they occurred (clinical interventions, diseases, donations, allergies, adverse reactions); and
    a second phase (B) comprising:
        identifying the data object stored in the data storage vault and the type of data stored by reading the public identification code to decode the binary data of the code for access to the information and the profiles of the data object stored in the data vault, based on the access permissions that are active when accessing the data, carried out through a camera or NFC sensor installed in an electronic device that runs a software application executed by a public user or by an entity and its authorized personnel or by a software service running in a computer system;
        generating, registering and automatically communicating an incident in case of existence of any impediment when making the identification, accessing the data, making the registration of new information, when a verification is required or when certain previously established conditions are met (variations in the temperature, close expiration, rejection of the product for some reason), carried out by the main computer system and/or by a software application running in an electronic device (server, computer or tablet, via email, SMS, push notification to a software application or by a logging service); and
        automatically updating the information in the vaults and profiles stored in the database accessible by the different parties with data on the process of obtaining, manufacturing, supplying and/or using (lot number, result of analysis performed, shipping/reception transactions, utilization in a clinical intervention, data of the individuals), carried out by the main computer system (via API REST or gRPC).

2. The method according to claim 1, wherein the method generates global public and private identifiers, unique and non-transferable, as well as the unique identification codes of products of biological origin, of individuals (human or other types), of cellular production lines, of entities (companies, organizations, donation centers, medical centers, clinics, hospitals, laboratories) as well as of the related personnel and devices, and of clinical interventions (medical in humans or veterinary in animals), carried out by the main computer system after a request is received and whose are stored in the global database and optionally in the regional databases (via API REST or gRPC).

3. The method according to claim 1, wherein the method uses the universal donor identifier as the universal identifier of individuals and for the traceability of the health history stored in the global and/or in the regional databases of all related individuals (donors, recipients, users, clients, patients).

4. The method according to claim 1, wherein the product identification code contains product identifiers from one or more countries (or jurisdictions), one or more product labeling systems and, additionally, one or more links to web addresses, stored in the global database and/or in the regional databases.

5. The method according to claim 1, wherein the identification code is deposited in a device that contains a unique identifier in an NFC tag or similar that identifies univocally the device, carried out by a software running in an electronic device configured for that.

6. The method according to claim 1, wherein the identification code is deposited in a QR code or similar types of matrix barcodes that can be displayed in the screen of an electronic device or printed and associated to the different parties, carried out by a software running in an electronic device configured for that.

7. The method according to claim 1, wherein the public identifier and the private identifier are generated using an URN format that allows to identify the type of data it refers to and includes an UUID in v4 format formed by 32 hexadecimal characters.

8. The method according to claim 1, wherein the public identifier, the private identifier and, additionally, other data contained in the identification code are available for automatic reading by electronic devices (Machine Readable Interpretation or MRI) and for Human Readable Interpretation (HRI) by means of a set of alphanumeric characters that avoid confusion among them by a bad reading and that are defined by an alphanumeric-hexadecimal translation map; additionally, the UUID of the public identifier can be converted to an UDI-DI compatible identifier both to Base 64 or to Base 58 to fit the maximum length requirements in different regulations.

9. The method according to claim 1, wherein the identification code contains public and private information and the access rights to the private information is managed by the main computer system and/or by the regional computer systems; a first type of public information (open accessibility) include the public identifier and other information variable in each case; a second type of information is accessible through the private identifier and only from centers and personnel with the required permissions to access this information; the private information can be additionally encrypted in the identification code and also in the global and/or regional databases to be accessible only by the authorized entities and personnel through an encryption key (using a symmetric or an asymmetric encryption key) which is required to decrypt the data for access the private information.

10. The method according to claim 1 further comprising:
automatically obtaining, during the process of collection, manufacture, supplying and utilization, the information related to each of the parties (production data, derived products, telemetry devices) and storing said information in the corresponding vaults and profiles in the global database, carried out by the main computer system (via API REST or gRPC);
sending a notification to the related and/or designated parties when the obtained data is available for consultation, carried out by the main computer system (via email, SMS, push notification to a software application);
obtaining relevant information from other entities (collection of reports, breakage of the cold chain), automatically incorporating this information into the data object and profiles stored in the global or local vaults, and notifying it to related parties and designated personnel, carried out by the main computer system or by one or several regional computer systems (via API REST and email, SMS, push notification to a software application); and
generating automatic alerts upon detecting certain conditions (close expiration, expiration of a product, detection of anomaly), to initiate protocols, request verification or validation of other data or related products that may be affected and incorporating said information to the corresponding data vaults and profiles of a data object, carried out by the main computer system or by one or several regional computer systems (via API REST and email, SMS, push notification to a software application, logging service).

11. The method according to claim 1 further comprising:
detecting and registering the location of a product through geolocation incorporated in it or through electronic devices to which it is associated (SIM card by mobile phone, geolocation device), carried out by the main computer system, by one or several regional computer systems or by a software application running in an electronic device (via API REST); and
generating a notice and reporting the location of a product to the owner and/or to the destination, as well as the expected delivery or arrival time of the product, carried out by the main computer system or by one or several regional computer systems (via API REST and email, SMS, and/or push notification to a software application).

12. The method according to claim 1, wherein when a transaction is made (sending/receiving, buying/selling, utilization in a clinical intervention) and new information is generated in the global and/or regional vaults after a transaction request received by the main computer system and processed by it, optionally the method further comprising:
checking that the conditions to carry out the transaction are met and notifying the parties (valid or compatible product, user authorized to write data in the database), carried out automatically by the main computer system after a request received (via REST API or gRPC, among others; and
updating the information of the data object in the corresponding vaults and profiles with the result of the transaction made, carried out by the main computer system after a response received from the global database (via REST API or gRPC).

13. The method according to claim 1, wherein the data communication between the local computer systems of the authorized centers, the electronic devices and the global and regional computer systems is carried out in a secure manner by using Secure Sockets Layer (SSL) and/or Virtual Private Networks (VPN).

* * * * *